(12) United States Patent
Gunes et al.

(10) Patent No.: US 8,753,655 B2
(45) Date of Patent: Jun. 17, 2014

(54) LIQUID-FILLED CHITOSAN-ANIONIC LIPOSOLUBLE SURFACTANT CAPSULE DISPERSIONS

(75) Inventors: Zeynel Deniz Gunes, Lausanne (CH); Matthieu Pouzot, Lausanne (CH); Raffaele Mezzenga, Zurich (CH); David Labbe, Lausanne (CH)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 13/578,460

(22) PCT Filed: Feb. 17, 2011

(86) PCT No.: PCT/EP2011/052363
§ 371 (c)(1),
(2), (4) Date: Aug. 10, 2012

(87) PCT Pub. No.: WO2011/101415
PCT Pub. Date: Aug. 25, 2011

(65) Prior Publication Data
US 2012/0315313 A1    Dec. 13, 2012

(30) Foreign Application Priority Data
Feb. 18, 2010   (EP) .................................... 10153926

(51) Int. Cl.
| A61K 8/02 | (2006.01) |
| A61K 9/48 | (2006.01) |
| A23D 7/00 | (2006.01) |
| A23D 9/00 | (2006.01) |
| A23C 9/12 | (2006.01) |
| A23L 1/30 | (2006.01) |

(52) U.S. Cl.
USPC ........... 424/401; 424/451; 426/601; 426/602; 426/61; 426/72

(58) Field of Classification Search
USPC ............... 424/401, 451; 426/601, 602, 61, 72
See application file for complete search history.

(56) References Cited

U.S. PATENT DOCUMENTS

| 8,137,728 | B2 | 3/2012 | McClements et al. | |
| 2005/0202149 | A1* | 9/2005 | McClements et al. | 426/601 |
| 2007/0104866 | A1* | 5/2007 | McClements et al. | 427/213.3 |
| 2012/0315313 | A1 | 12/2012 | Gunes et al. | |

FOREIGN PATENT DOCUMENTS

| CN | 1997282 | 7/2007 |
| CN | 101288662 | 10/2008 |
| CN | 101444495 | 6/2009 |
| EP | 1358872 | 11/2003 |
| EP | 2536297 | 12/2012 |

OTHER PUBLICATIONS

Ogawa et al., Cationic Droplets Stabilized by Lecithin-Chitosan Membranes, J. Agric. Food Chem., 2003, 51, 2806-2812.*
L. A. Shaw et al. Spray-Dried Multilayered Emulsions as a Delivery Method for omega-3 Fatty Acids into Food Systems. J. Agric. Food Chem., 2007, 55, 3112-3119.*
Henriksen, et al. "Interactions between liposomes and chitosan." Department of Pharmaceutics, International Journal of Pharmaceutics, vol. 101, No. 3, Jan. 25, 1994, pp. 227-236, XP-002591771.
Magdassi, et al. "Formation of positively charged microcapsules based on chitosan-lecithin interactions." Journal of microencapsulation, vol. 14, No. 2, 1997, pp. 189-195, XP-00259-1769.
Ogawa, et al.: "Production and characterization of O/W emulsions containing cationic droplets stabilized by lecithin-chitosan-pectin mutilayered membranes."Journal of agricultural and food chem. vol. 51, No. 9, Apr. 23, 2003, pp. 2801-2812, XP-002323017.
Ogawa et al.: "Production and Characterization of O/W emulsions containing droplets stabilized by lecithin-chitosan-pectin multilayered membranes."Journal of Agricultural and Food Chemistry 2004, 52, 3595-3600, XP-0025911767.
Klinkesorn, et al. "Encapsulation of emulsified tuna oil in two-layered interfacial membranes prepared using electrostatic layer-by-layer deposition." Food Hydrocolloids, vol. 19 No. 6, Nov. 2005 pp. 1044-1053, XP-002591768.
Mun, et al. Influence of droplet characteristics on the formation of oil-in-water emulsions stabilized by surfactant-chitosan layers, Langmuir 2005, vol. 21, No. 14, XP-02591770.
Park, et al. Influence of encapsulation of emulsified lipids with chitosan on their in vivo digestibility, Food Chemistry, vol. 104, No. 2, 3, May 2007, pp. 761-767, XP022055358.
PCT International Search Report for Application No. PCT/EP2011/052363 with a mailing date of Nov. 5, 2011. 5 Pages.
Written Opinion of the PCT International Searching Authority for Application No. PCT/EP2011/052363 with a mailing date of Nov. 5, 2011. 9 Pages.

\* cited by examiner

*Primary Examiner* — Gina C. Yu Justice
*Assistant Examiner* — Genevieve S Alley
(74) *Attorney, Agent, or Firm* — K&L Gates LLP (57) ABSTRACT

The present invention generally relates to the field of membranes. In particular, the present invention relates to a composition comprising bodies surrounded by a membrane. The composition are for example edible compositions. One embodiment of the present invention relates to a composition containing an oily fraction, a hydrophilic fraction, and at least one body, wherein the body comprises a shell comprising several molecular layers of chitosan and at least one lipidic phosphatidic acid surfactant; and a content comprising an internal phase containing a hydrophilic component and/or a hydrophobic component. The Composition may be used to protect a food product or to deliver specific properties to a product, for example.

16 Claims, 5 Drawing Sheets

LIQUID-FILLED CHITOSAN-ANIONIC LIPOSOLUBLE SURFACTANT CAPSULE DISPERSIONS

CROSS REFERENCE TO RELATED APPLICATIONS

The present application is a National Stage of International Application No. PCT/EP2011/052363, filed on Feb. 17, 2011, which claims priority to European Patent Application No. 10153926.0, filed on Feb. 18, 2010, the entire contents of which are being incorporated herein by reference.

The present invention generally relates to the field of membranes. In particular, the present invention relates to a composition comprising bodies surrounded by a membrane. The compositions are for example edible compositions. One embodiment of the present invention relates to a composition containing an oily fraction, a hydrophilic fraction, and at least one body, wherein the body comprises a shell comprising several molecular layers of complexant molecules, the complexant molecules being chitosan and at least one lipidic phosphatidic acid surfactant; and a content comprising an internal phase containing a hydrophilic component and/or a hydrophobic component. The composition may be used to protect a food product or to deliver specific properties to a product, for example.

Hollow oil-in-water or water-in-oil capsules of controlled size and thickness for controlled delivery purposes are usually produced by the process of layer-by-layer adsorption of (poly)ionic species on the droplets of an emulsion (Sukhishvili S. A., Curr. Op. Coll. Int. Sci. 2005, 10, 37; Grigoriev D. O., Miller R., Curr. Op. Coll. Int. Sci. 2009, 14, 48; Peyratout C. S., Dähne L., Angew. Chem. Int. Edit. 2004, 43, 3762). That is a tedious multi-step process which is time-consuming, and most often involves washing steps between two successive adsorption steps with alternating sign of electrostatic charge (Decker G., Eckle M., Schmitt J., Struth B., Curr. Op. Coll. Int. Sci. 1998, 3, 32), depending on the application. Consequently, interfaces formed using the layer-by-layer method are in most cases thin and mechanically weak.

The main advantage of the layer-by-layer method is that it allows building a tailored composite multi-layer structure, forming the shell of a hollow capsule. Other methods reported that allow for a certain degree of control on the shell thickness are based on the use of a multiple emulsion, or on phase separation at o/w interface (Grigoriev D. O., Miller R., Curr. Op. Coll. Int. Sci. 2009, 14, 48).

As for coacervation methods, their main drawback is the high sensitivity to process parameters and the inhomogeneous shell thickness. A uniform and controlled shell thickness can be achieved by interfacial polymerisation between small or polymeric surfactants, however, these methods usually require the removal of non-food organic solvents and monomers. A consequence of this is that the resulting capsules are generally not applicable for food-grade products.

For example, U.S. Pat. No. 5,843,509 describes the formation of submicron capsules using chitosan and oil-soluble lecithin by using acetone as an organic solvent.

Chitosan was shown to form hollow capsules based on electrostatic interactions, by the coating of liposomes (Henriksen, I.; Smistad, G.; Karlsen, Int. J. Pharm. 1994, 101, 227; Ogawa S., Decker E. A., McClements D. J., J. Agr. Food Chem. 2003, 51, 2806), as described also e.g. in U.S. Pat. No. 5,843,509, or by self-assembly when mixing a solution of an anionic emulsifier with a solution of chitosan (Gerelli Y., Barbieri S., Di Bari M. T., Deriu A., Cantù L., Brocca P., Sonvico F., Colombo P., May R., Motta S., Langmuir 2008, 24, 11378), but always for shell thickness below 100 nm (in the wet state), and generally by using non-food organic solvents.

It was the object of the present invention to improve the state of the art and, in particular, to provide a food grade composition comprising capsules with a controllable wall thickness of at least 100 nm to above that thickness.

For oil-in-water or water-in-oil emulsions, thickness control of the capsule walls was never achieved for large values, i.e. for wall thickness from about 100 nm to 1 mm.

Hence, the present inventors were surprised to see that they could provide a composition that can be fabricated in one facile step and that comprises food-grade capsules of tuneable composition, size, and shell thickness from 100 nm to the millimeter range, based on the interfacial complexation between ionic species forming a membrane at oil/water interface.

Consequently, the present inventors could achieve the object of the present invention by the subject matter of the independent claims. The dependent claims further develop the idea of the present invention.

The inventors describe a method that uses chitosan to fabricate in one facile step, food-grade capsules of tuneable composition, size, and shell thickness, based on the interfacial complexation between ionic species forming a membrane at oil/water interface.

More specifically, chitosan forms a complex with a lipidic phosphatidic acid surfactant.

The present method allows forming water-in-oil and oil-in-water capsules, and enables the encapsulation of certain oil-soluble or water-soluble small molecules, such as flavours.

The capsule size is set by the emulsification step when mixing oil and water, as was observed using microfluidic and batch emulsification methods. Its thickness can be controlled finely between a few nanometers up to the millimeter scale. High thickness values result in very high viscoelastic moduli (in shear, it can reach more than 1 Pa·m). Nevertheless the shell in the wet state remains to be highly flexible.

Consequently, if used in cosmetic or food products, the presence of capsules with a wall thickness in the micrometer range or smaller will not result in unwanted sensorial properties, such as grittiness.

Hence, one embodiment of the present invention is a composition containing an oily fraction, a hydrophilic fraction, at least one body, wherein the body comprises (1) a shell comprising at least 5 molecular layers of complexant molecules and (2) a content comprising an internal phase containing a hydrophilic component and/or a hydrophobic component. The shell thickness can be controlled via cryo-SEM or cryo-TEM methods. In the wet state the shell thickness is about 100 nm or larger.

The complexant molecules may be chitosan and at least one lipidic phosphatidic acid surfactant.

Typically, the lipidic phosphatidic acid surfactant content amounts to at least 20% w/w of all lipidic surfactants present in the shell.

The lipidic phosphatidic acid surfactant content may also amounts to at least 50% w/w of all lipidic surfactants present in the shell.

For example, no more than 0.1 weight-% of chitosan may present in solubilised state in the oily fraction of the composition and/or no more than 10 weight-% of lipidic phosphatidic acid surfactants may present in solubilised state in the hydrophilic fraction of the emulsion.

The chitosan and at least one lipidic phosphatidic acid surfactant may be complexed at the supramolecular level. This complexation contributes to the stability of the shell.

The resulting body may have a positive, a negative or no net charge.

Positive or negative net charges have the advantage, that the body can be functionalized by compounds with an opposite charge or that the bodies can be separated from the composition by charge separation. It may also contribute to avoid colloidal aggregation of capsules. Negative charge may be used to avoid undesired astringency in food products, depending on the food matrix, and the concentration and size of the capsules.

A neutral net charge has the advantage that the body will remain an integral part of the composition, even if it is contained in containers which may already have or develop a positive or negative charge, for example if friction is applied to the container.

The composition may be produced without the use of organic solvents except food-grade oils. Hence, the composition of the present invention does not contain non-food organic solvents or residues thereof. This of course has the advantage that the composition may be easily used for cosmetic or food applications, without the need to remove non-food organic solvents and without the risk of having some residual said organic solvents present in the composition.

Organic solvents are solvents containing carbon. For example, the composition of the present invention may be prepared without the use of organic solvents and/or does not contain organic solvents with a boiling point below 100° C., 90° C. or 80° C.

Chitosan is a natural compound which has a polysaccharide backbone, is derived from chitin, sources of which are crustacean shells or fungi, and is water-soluble below a certain pH where its polycationic character will help its dissolution.

The composition of the present invention may be any kind of composition. Preferably it is a food grade composition or a food product.

For example, the composition may be an emulsion, e.g. a sub-micro-emulsion, a micro-emulsion or a macro-emulsion.

The emulsion may also be a double emulsion, e.g., for low calorie applications.

The emulsion may further be an ISAmulsion. ISAmulsions are for example described in detail in USPTO Patent Application 20080255247. The term 'ISAmulsion' describes the specific nature of the oil droplets containing a structure being Internally Self-Assembled, which is different from ordinary oil-in-water or w/o/w double emulsions, including nano- and microemulsions, in which the oil droplets do not have a nano-sized self-assembled structure with hydrophilic domains. The ISAmulsion droplets basically consist of oil droplets which have a self-assembled structure with hydrophilic domains. This structure can be of a lamellar liquid crystalline, or a lamellar crystalline, or of a reversed nature comprising the L2, the microemulsion, the isotropic liquid phase, the hexagonal, the micellar cubic, or the bicontinuous cubic phase. The structures in the oil phase can appear as a single nano-structure or as a mixture of different nano-structures.

Emulsions have the advantage that they are pleasant to consume and offer an attractive mouthfeeling.

Sub-micro emulsions have the advantage that they are optically transparent and have no cloudy appearance.

Depending on the intended purpose micro- or macro-emulsions may be preferred because each of these emulsions offer specific organoleptic properties.

The at least one body may be a substantially round capsule, an elongated capsule, a flat-shaped capsule or a fibre. The method of the present invention allows adjusting the shape of the body according to the needs.

If it is desired to use the body to transport or protect valuable oily or hydrophilic compounds a substantially round or round shape may be preferred, because this shape allows it to contain a maximum amount of content per surface.

Elongated capsules, flat shaped capsules of fibres offer the advantage of a large surface. This is in particular useful, if the surface is going to be functionalized. Moreover, the hydrodynamic interactions can be greatly increased within the emulsion owing to non-spherical capsule shapes, which makes these shapes suitable for controlling the product viscosity and texture.

The body contains an internal phase. This internal phase may represent at least about 0.01 Vol-%, preferably at least about 50 Vol-%, even more preferred at least about 90 Vol-% of the content of the body. For, example, the body may be filled completely with the internal phase.

The internal phase may consist of a single compound or may contain a mixture of compounds.

For example the internal phase may comprise one or more hydrophilic components. A hydrophilic component of the internal phase may be liquid or gaseous. Such physical conditions refer to room temperature and standard pressure.

Hydrophilic components may be selected from the group consisting of hydrophilic liquids, such as water, fruit juices, lemonades, alcoholic beverages, coffee liquors, coffee extracts, flavoured waters, proteins in solution or dispersion, enzymes in solution or dispersion, water-soluble vitamins in solution; or combinations thereof.

The internal phase may alternatively or additionally comprise one or more hydrophobic components. A hydrophobic component of the internal phase may also be liquid or gaseous.

For example, the internal phase may contain hydrophobic components selected from the group consisting of flavoured and/or fragranced oils, for example mint oil; essential oils; fish oil; oily compounds comprising omega-3 fatty acids; and/or omega-6 fatty acids.

Consequently, the bodies of the present invention may be used for several purposes. For example, they may be used
  to protect valuable food ingredients, for example, from oxidation,
  to avoid that functional ingredients, e.g., enzymes, are in direct contact with a food product,
  to mask undesired off-tastes,
  to avoid unwanted odour generation,
  to impart a specific taste to a product,
  to impart a specific mouthfeel to a product,
  to provide a specific texture in a product, or
  to provide a stable dispersed structure in e.g. bouillons, by using the capsules to encapsulated oil drops, possibly with flavours, and removing the excess of water.

The shell of the body may comprise chitosan and at least lipidic phosphatidic acid surfactant. The shell may also contain other polyelectrolytes, such as proteins, for example.

The shell may also consist of chitosan and a lipidic phosphatidic acid surfactant.

Chitosan and the at least one amphiphilic surfactant may be present in any proportion that allows the formation of a stable shell. Suitable proportions may be determined by those skilled in the art by using routine experimentation.

For example, chitosan and the at least one amphiphilic anionic lipidic surfactant may be used in a weight ratio in the range of 1:10 to 10:1, preferably 5:1 to 1:1.

The lipidic phosphatidic acid surfactant may have a partition coefficient (water/oil) smaller than 1:100 in ambient conditions. Such anionic lipidic surfactants have the advantage that they will be present almost exclusively in the oily fraction in soluble state and/or at the oil/water interface of the composition, provided that the volume fraction of the dispersed oil phase is sufficiently high. For example, lipidic phosphatidic acid surfactants may be e.g. an ammonium phosphatidic fatty acid, or a mixture of phosphatidic acids comprised, e.g., in lecithin, preferably lecithin YN.

For example, the shell of the body may comprise chitosan and lecithin. In a further example, the shell of the body may comprise chitosan and lecithin YN.

The method of the present invention allows producing bodies with a surprisingly thick and hence durable shell. Consequently, the diameter of the shell in the wet state may be in the range of about 100 nm to 1000 μm, preferably about 300 nm to 3 μm, more preferred about 500 nm to 1 μm. The choice of the shell thickness will allow achieving the correct property desired, e.g. for encapsulation and/or for mechanical protection of the internal phase.

The body described in the present invention may comprise chitosan in the range of about 0.0001-80 weight-%, preferably in the range of about 0.01-1 weight-%, even more preferred in the range of about 0.01-0.3 weight-%.

If the chitosan content of the body of the present invention is high, e.g., in the range of 10-80 weight-%, this allows the preparation of bodies that—if removed from the composition—have a dry appearance although they contain a liquid core.

Hence, the present invention also relates to a body, comprising 10-80 weight-% of chitosan and at least one lipidic phosphatidic acid surfactant, and a content comprising an internal phase containing a hydrophilic component and/or a hydrophobic component.

The bodies described in the present invention may further comprise particles that adsorb on a water/oil interface, encasted in its shell and protruding at the hydrophobic side of the shell.

Particles that attach to the water/oil interface of the shell irreversibly due to high interfacial energy gain are entrapped at the surface of the shell allowing for further applications. The capsule or membrane can then be seen as having a functionalized surface, the surface layer of particles hence may be used for controlling physical and chemical interactions with the environment.

Such particles may be any particles that deliver a desired property to the body. For example, such particles may be selected from the group consisting of coloring agents, tastants, antioxidants, antibacterial agents, radical scavengers, fat particles, mineral particles, charged molecules, and combinations thereof.

The composition of the present invention may in principle be used to prepare any kind of product the bodies described in the present invention are considered beneficial for.

For example, the composition of the present invention may be used for the preparation of a food composition, an animal food composition, a pharmaceutical composition, a cosmetic composition, a nutraceutical, a drink, a food additive or a medicament.

The composition of the present invention and/or the bodies described in the present invention offer many advantages as already discussed.

For example, the composition of the present invention and/or the bodies described in the present invention may be used to stabilize emulsions.

The bodies of the present invention exhibit a remarkable stability, which will contribute to the emulsion stability. Further, the surface of the bodies may be functionalized with agents that serve themselves to stabilize emulsions, such as emulsifiers.

The composition of the present invention and/or the bodies described in the present invention may be used to stabilize any kind of emulsions, for example, water in oil (w/o) or oil in water (o/w) emulsions, double emulsions (w/o/w, or o/w/o) or IS Amulsions.

The composition of the present invention may impart many different features and/or functionalities to a product. Essentially this may be achieved by the content of the bodies, by the functionalization of the shell surface of the bodies or by a combination of both means.

For example, the composition of the present invention and/or the bodies described in the present invention may be used to for the preparation of a product with a longer lasting flavour perception.

Advantageously, after oral consumption the bodies described in the present invention will be in contact with the tongue much longer than normal tastants present in a food composition. Tastants, such as mint oil for example, will be released slowly and on site from the content of the bodies, when chewing, for example.

Additionally or alternatively the composition of the present invention and/or the bodies described in the present invention may be used to provide an improved flavour conservation, and/or fragrance conservation.

If present in the bodies or as a functional part of the surfaces of the bodies flavour and/or aroma compounds are significantly less volatile and will remain within the product for significantly longer time periods. They are also protected from unwanted reactions, such as oxidation, for example.

If a tastant or fragrance that provides a refreshing effect is used, the refreshing effect will be improved, because the perceived intensity will be increased and the effect will be prolonged. Tastants or fragrances providing refreshing effects may be mint oil or citrus oils, such as lemon, lime, orange or grapefruit oils, for example. Other etheric oils may be equally well be used.

The composition of the present invention and/or the bodies described in the present invention may be also be used to provide a moisture barrier, for example. In particular, if the bodies have a fibrillar or flat shape, they may be used to protect a product from moisture loss, for example. The bodies will then form a membrane like structure which protects a product.

The composition of the present invention and/or the bodies described in the present invention may be also be used to provide an anti-microbial and/or an antifungal activity. The bodies described in the present invention, in particular if they have a flat or fibrillar shape may serve as a moisture barrier. As such, they will automatically prevent microbial or fungal colonization of the product.

Alternatively or additionally, the bodies of any shape may be filled with an antimicrobial and/or antifungal agent. Alternatively or additionally the surface of the shell may be functionalized with an antimicrobial and/or antifungal agent. Such bodies will be effective if they are mixed with a product and also if the composition covers the surface of a product to be protected from microbial or fungal contamination.

The composition comprising the bodies described in the present invention may be prepared by a method comprising the steps of combining the at least one lipidic phosphatidic acid surfactant with the oily fraction to produce a solution A; and combining chitosan with the hydrophilic fraction to produce a solution B.

Here typically the amount of the at least on one lipidic phosphatidic acid surfactant in the oily fraction is in the range of 0.01% to 1% w/w and the pH may be adjusted to a range of 1.5 to 6.5.

The typical amount of chitosan in the hydrophilic fraction is in the range of 0.01% to 1% w/w and the pH may be adjusted to a range of 1.5 to 6.5.

Then either solutions A and B are mixed to prepare dispersion C1; or a dispersion D is prepared of solution A and a hydrophilic solvent and then dispersion D is mixed with solution B to prepare dispersion C2, or a dispersion E is prepared of solution B and a hydrophobic solvent and then dispersion E is mixed with solution A to prepare dispersion C3.

In dispersion C1, A and B may be used in a volume proportion range of 1:1000 to 1:2.

In dispersion D, A and a hydrophilic solvent may be used in a volume proportion range of 1:1000 to 1:2. The pH may be adjusted to a range of 1.5 to 6.5.

In dispersion C2, D and B may be used in a volume proportion range of 1:1000 to 1:2.

In dispersion E, B and a hydrophobic solvent may be used in a volume range of 1:1000 to 1:2. The pH may be adjusted to a range of 1.5 to 6.5.

In dispersion C3, E and A may be used in a volume range of 1:1000 to 1:2.

Then a membrane is allowed to form which will represent the shell of the bodies of the present invention.

Membrane growth may be stopped by means known to those skilled in the art.

If the chitosan solution is the continuous phase membrane growth may for example be stopped by flocculation of the solubilised chitosan—e.g. with anionic water-soluble compounds—, or by adjusting the pH to a value of above 7, and/or by washing out the chitosan from the continuous phase—e.g. using concentration of the capsules and re-dispersion, or dialysis.

In the case where the lipidic solution is the continuous phase membrane growth may be stopped by washing out the anionic lipidic emulsifier from the continuous phase—e.g. using concentration of the capsules and re-dispersion, or dialysis.

The resulting shape of the bodies will be essentially spherical. If a different body shape is desired, flowing, shearing, or squeezing forces may be applied to dispersions C1, C2 or C3. Using such forces flat or elongated shapes may be obtained.

Both, the size of the bodies as well as the thickness of the shells may be controlled.

This may be important if the bodies are used for controlled delivery purposes.

Shell thickness and the body size are parameters that can be used to fine-tune the body for the intended purpose. Since high mechanical properties of the shell can be achieved by choosing the appropriate thickness, e.g., oil-in-water capsules are good candidates for being turned to a powder by for example spray-drying. Other methods of drying can also be used.

The swelling degree of the wet shell can be influenced by pH, osmotic pressure, and the difference between the pH values at the fabrication stage and at the use stage.

The proposed method can also be used in combination with a specific choice as for the inner phase of the capsules, which may e.g. increase its mechanical strength, or add control parameters to controlled release.

Furthermore, the use of fat particles entrapped at the shell surface, for example, enables the control the shell wetting properties. Colloidal properties of the bodies described in the present invention, as well as mechanical interactions with bodies or molecules of a different nature, will depend on the choice of the particles and on the environment of use, as well as on the size of the bodies and the flexibility of the shell.

The presence of the particles on the shell will not affect significantly the encapsulation properties, since the membrane continuity is maintained at the same lengthscale.

It is clear to those skilled in the art that they can freely combine all features described in the present application without departing from the scope of the invention as disclosed.

Further advantages and features of the present invention will be apparent from the following Examples and figures.

EXAMPLES

Microfluidics Methods to Evidence Control on Capsule Size

A microfluidic flow-focusing geometry allowed fabricating monodisperse capsules with controlled size (Xu S., Nie Z., Seo M., Lewis P., Kumacheva E., Stone H. A., Garstecki P., Weibel D. B., Gitlin I., Whitesides G. M., Angew. Chem.

Figure 1:
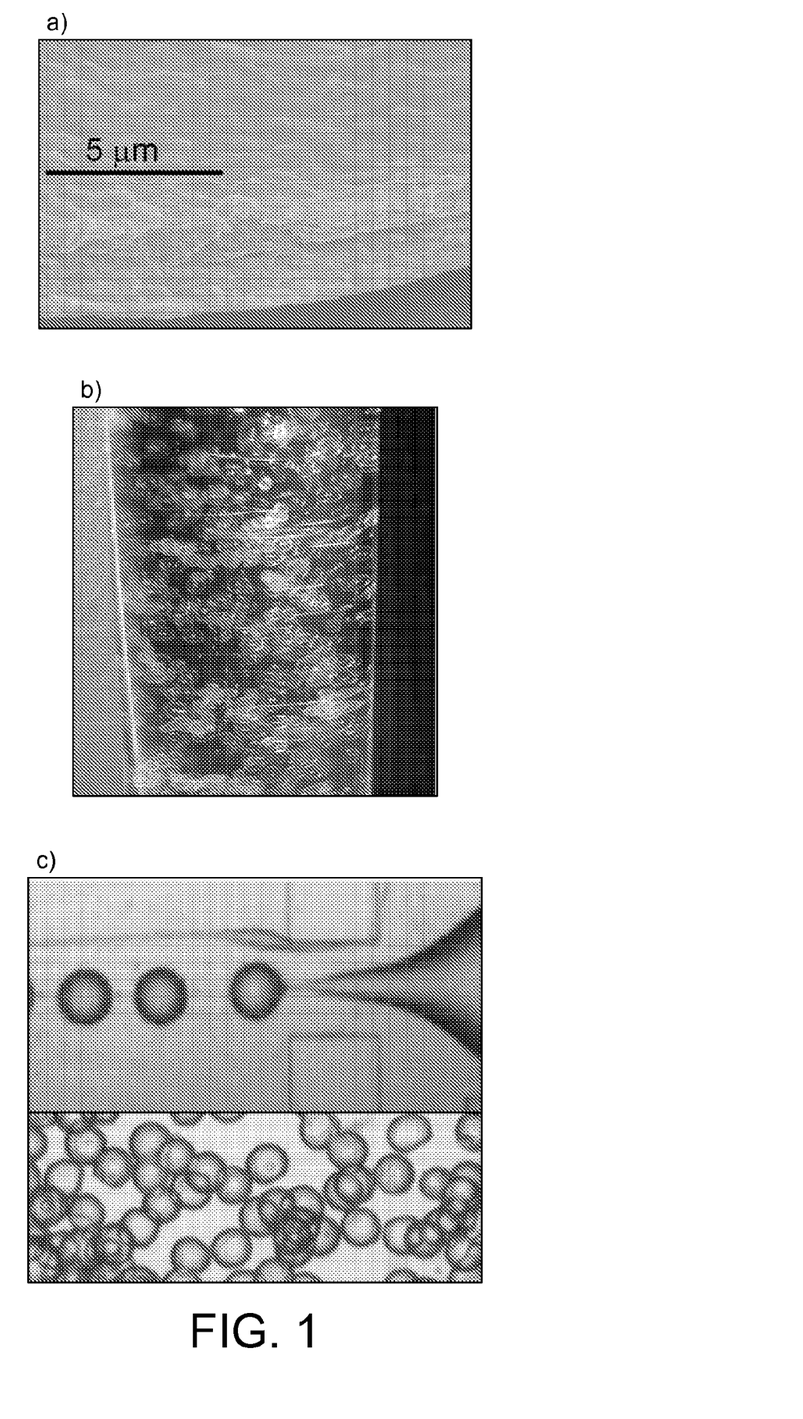
FIG. 1a shows SEM observation of a shell formed with chitosan (0.24% w/w, Mw=300,000 g/mol, 80% deacetylation) and lecithin YN at pH 3. SEM also reveals that the membrane is highly homogeneous in thickness, and not porous at the smallest observed scale, being around 10 nm.
FIG. 1b shows monodisperse capsules formed using microfluidic methods (diameter 250 µm), floating in ethanol (after washing away the oil phase).
FIG. 1c shows monodisperse capsules formed using microfluidic methods (diameter 250 µm).

Int. Edit. 2005, 200544, 724), both for water-in-oil and oil-in-water systems. Monodisperse capsules could be formed using microfluidic methods, and their chemical and physical stability investigated and collected for observation. Hydrophobic polymeric microfluidic chips ThinXXs AG (Germany) were used for generating water-in-oil emulsions, and hydrophilic glass chips from by Micronit BV (the Netherlands) were used for generating oil-in-water emulsions (FIG. 1c).

Evidence of Interfacial Complexation at Oil/Water Interface by Dynamic Interfacial Tension Measurements Interfacial Tension Measurement Method:

The interfacial tension measurement versus contact time between the oil and water phases, was performed using a pendant drop method (Tracker, Teclis, France). The drop is pending from a cylindrical capillary, and the shape of the drop, as well as the contact angle on the capillary, are recorded at any time. The interfacial tension is inferred by fitting the drop shape in equilibrium in the presence of capillary and gravity forces.

Figure 2:
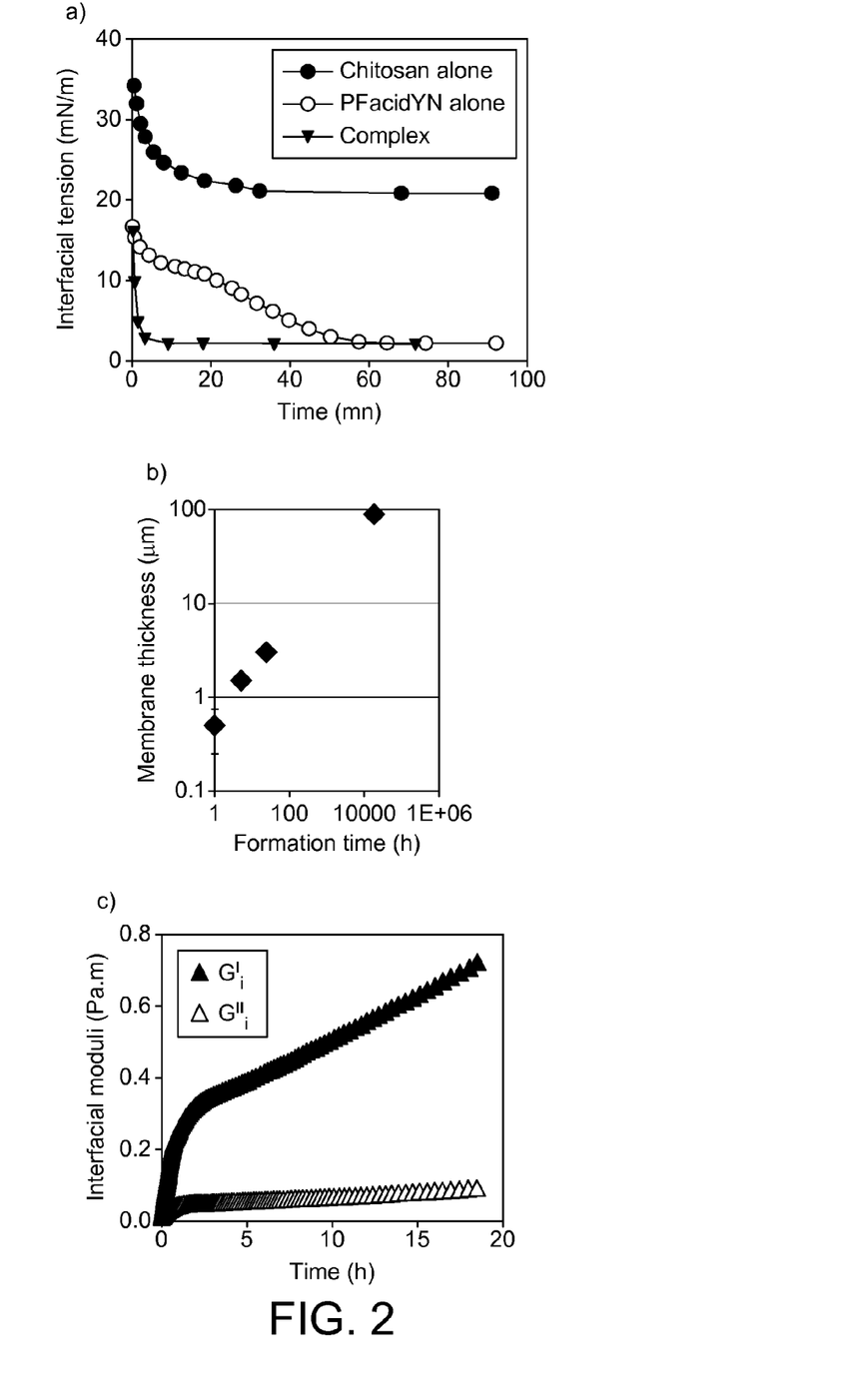
FIG. 2a shows the dynamic interfacial tension at oil/water interface for: i) water/MCT solution with lecithin YN 0.5% w/w; ii) chitosan solution 0.24% w/w/MCT oil; iii) chitosan solution 0.24% w/w/MCT oil with lecithin YN 0.5% w/w.
FIG. 2b shows the membrane thickness as determined from SEM images, for standard concentrations (chitosan solution 0.24% w/w/MCT oil with lecithin YN 0.5% w/w) and pH 3, versus formation time.
FIG. 2c shows linear shear interfacial moduli during membrane formation (0.1 Hz), for standard concentrations (chitosan solution 0.24% w/w/MCT oil with lecithin YN 0.5% w/w) and pH 3 at 23° C., at 0.1 Hz.

At the interface of the chitosan solution and the lecithin YN solution in oil, electrostatic complexes formation takes place as soon as the first complexant molecules, i.e. of chitosan and lecithin YN, have reached the interface, as shown by dynamic interfacial tension measurements using a pendant drop method. In the presence of both chitosan and lecithin YN, the contrast with the cases where either chitosan or lecithin YN is absent is striking, whereby the interfacial tension drops below 3 mN/m within a time of the order of 10 s, which is 100 times more rapid than for lecithin YN alone, and demonstrates the formation of the interfacial membrane (FIG. 2a).

Control of Shell Thickness

The shell thickness was measured after drying of the capsule, using SEM microscopy.

The shell thickness can be controlled finely, using concentration and formation time. Small thickness values will be achieved by choosing low complexant concentrations and shorter formation times. The thickness can reach values of several hundreds of microns in the wet state after a year of formation time, corresponding to tens of microns in the dry state. It should be noted that upon drying out, the shell volume shrinks by a factor 10 if initially in wet conditions (e.g. pH 3 in contact with water). Over long times, the shell thickness increases as the square root of time in the absence of strong convective motions, suggesting a diffusion-controlled mechanism to be dominant.

Mechanical Properties of the Capsule Shell

Method of Mechanical Characterisation of the Shell by Interfacial Shear Rheology:

The linear shear interfacial viscoelastic moduli $G'_i$ (storage) and $G''_i$ (loss) of a membrane forming at a flat oil/water interface were characterised (typically at 0.1 Hz) as a function of formation time. The equipment used for recording linear viscoelastic properties of the membrane is an interfacial rheology cell from Anton Paar Physica (Germany), and we used a method to subtract the contribution of the bulk phases, as predicted by Boussinesq (Boussinesq. M., *Ann. Chim. Phys.* 1913, 29, 349).

Typical Observations:

The membrane develops an elastic character within a couple of minutes in the conditions shown in the figure below, and its elasticity (i.e. $G'_i/G''_i$) increases during the first 3 to 4 hours. Very high moduli are reached rapidly, compared to both the levels of an interface consisting of adsorbed chitosan only (based on the same concentration), and of an interface consisting of adsorbed lecithin YN (idem), at any waiting time. When the shear modulus achieves the order of 1 Pa·m, the membrane can be easily manipulated with tweezers, displaying high flexibility when in liquid environment and in contact with water (i.e. not dry), i.e. they bend and fold very easily.

Even when dried out, glassy films are very flexible when their thickness is of the order of a micrometer, whereas thicker films of tens of micrometers are stiff and brittle.

Capsule Chemical and Physical Stability

The reaction of the membrane to various chemical and physical stresses was tested. The membrane could be recovered in distilled water or solvent such as ethanol or acetone, and retained its integrity and shape over several months at room temperature. The same was observed in acidified or alkaline water in the window of pH 2-14, with at least two years of stability in the pH range 3-14. In contrast, for pH 1 the membrane fell into pieces after a couple of days. It was also observed that the capsules can be formed at temperatures of 40 or 50° C. at pH 3, thus certainly such temperatures do not damage the shell. Capsule integrity was retained after freezing down to −20° C., and re-melting by heating.

Structure in the Chitosan/Lecithin Shells

Figure 3:
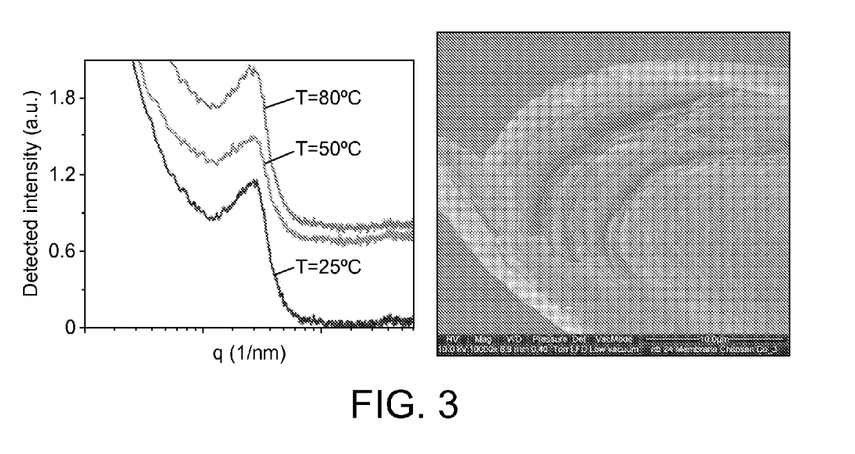
FIG. 3 shows on the left Small Angle X-ray Scattering signatures of the dry membrane, for temperatures of 25° C., 50° and 80° C. and on the right an image showing like a multi-sheet organisation of the torn membrane.

Small Angle X-ray Scattering curves, determined at different temperatures for the dry membrane, all show a broad peak for a characteristic lengthscale of 4.8 nm. This is actually a value of the order of a fatty acid bilayer thickness and of the order the thickness of lamellar structures observed in self-assembled chitosan-lecithin capsules, in solution. Besides, SEM images of the torn dry membrane show a multi-sheet organisation, as it could be easily peeled into a number of thinner sheets, suggesting a lamellar growth parallel to the membrane (FIG. 3).

Formation of Chitosan/Lecithin YN Capsules

Materials

Figure 4:
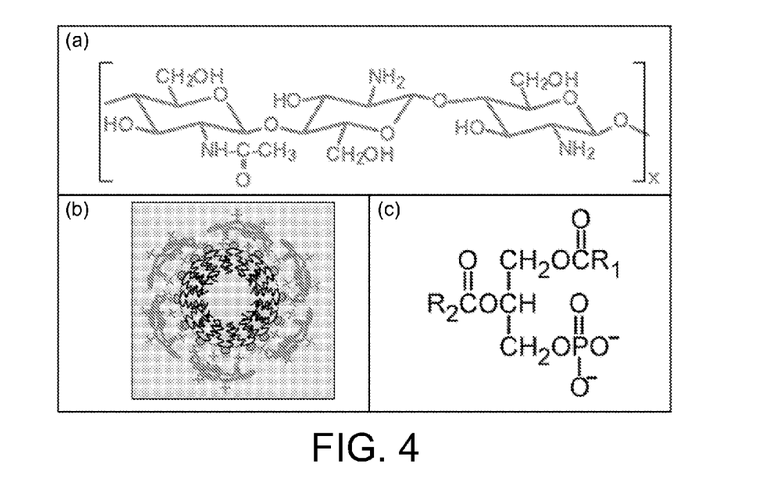
FIG. 4 (a) shows the chemical structure of chitosan. (b) shows a sketch of the first layer formed by chitosan/anionic emulsifier complexation at the interface of a water-in-oil drop. (c) shows a typical chemical structure of lipidic phosphatidic acid molecules.

Chitosan (CAS number 9012-76-4) is a carbohydrate polymer obtained from the deacetylation of chitin (poly-b-1,4-D-N-acetylglucosamine) by alkali treatment, with generic structure shown in FIG. 4a. Its structure depends on its degree of deacetylation, generally comprised between 60% and 99% (100% deacetylation would yield poly(D-glucosamine)). This sets the electrostatic charge density.

The ammonium phosphatidic fatty acid used is comprised in a commercial lecithin known as lecithin YN, purchased from Palsgaard (Palgaard®4448, food-grade E442, commonly used as viscosity modifier in chocolate formulations). The generic chemical structure of the phosphatidic acids in lecithin YN is sketched in FIG. 4c in its anionic form. The phosphatidic acids represent more than 50% of all lipidic emulsifiers comprised in lecithin YN. In FIG. 4c, at least one of the groups R1 or R2 is a fatty acid moiety, otherwise a hydrogen atom, and one the counter-ions is ammonium (not shown). Lecithin YN and is insoluble in water at any temperature. It is soluble in common food oils and melted fats up to several grams per liter. The main pKa values of the phosphatidic acid molecules in lecithin YN are 3.0 and 8.0, so when adsorbed at oil/water interface with pH around 3 or higher, the molecules carry a significant fraction of negative charges; that fraction is 0.25 at pH 3. At pH below the pKa of the chitosan chains, the major part of the acido-basic groups of chitosan are charged.

Capsules Formation

1. A chitosan solution of concentration in the range 0.1-1% w/w is prepared by dispersion of a chitosan powder in water (average molecular weight Mw in the range 100,000 to 500,000 g/mol), deacetylation degree in the range 60-80%). Chloride acid is used to achieve proper dissolution, to set the pH at 3 (ideally).

2. Lecithin YN from is dissolved in mid-chain-triglyceride oil at a concentration in the range 0.1-0.5% w/w.

3. An emulsion is formed by dispersing the lecithin YN oil solution formed in (2) in water at pH 3, for oil to water volume proportion typically in the range 1%-40%, using a mechanical dispersion method, typically a high-speed rotor-stator (of e.g. Polytron brand type).

4. The emulsion formed in (3) is mixed with the chitosan solution prepared in (1) in 1:1 weight proportions, by soft mechanical mixing.

5. The dispersion formed in (4) is left in quiescent state or kept under gentle mechanical stirring, which leaves the interfacial shell to grow in thickness.

6. In the dispersion formed in (5), the capsule shell growth is stopped by setting the pH in the aqueous phase to 7 using sodium hydroxide.

7. The dispersion of capsules can subsequently be dried or spray-dried to be used in water-free or in water-poor formulations. They can be used as alternatives for encapsulation formulations in e.g. bouillons. The preferred capsule thickness is in such cases above 1 micrometer and allows achieving high enough mechanical strength needed for such applications.

Formation of Chitosan/Lecithin Water-in-Oil Capsules

Water-in-oil capsules can be formed by performing the exact symmetric protocol of Example 1 by changing the role of the oily and aqueous phases, as described hereafter.

1. A chitosan solution of concentration in the range 0.1-1% w/w is prepared by dispersion of a chitosan powder in water (average molecular weight Mw in the range 100,000 to 500,000 g/mol), deacetylation degree in the range 60-80%). Chloride acid is used to achieve proper dissolution, to set the pH at 3 (ideally).

2. Lecithin YN from is dissolved in mid-chain-triglyceride (MCT) oil at a concentration in the range 0.1-0.5% w/w.

3. An emulsion is formed by dispersing the chitosan solution formed in (1) in mid-chain-triglyceride oil, for water to oil volume proportion typically in the range 1%-40%, using a mechanical dispersion method, typically a high-speed rotor-stator (of e.g. Polytron brand type).

4. The emulsion formed in (3) is mixed with the lecithin YN solution prepared in (2) in 1:1 weight proportions, by soft mechanical mixing.

5. The dispersion formed in (4) is left in quiescent state or kept under gentle mechanical stirring, which leaves the interfacial shell to grow in thickness.

6. In the dispersion formed in (5), the capsule shell growth is stopped by successive centrifugation/redispersion steps, with redispersion in pure MCT oil, until the concentration in lecithin YN is low enough for the formation kinetics to be practically stopped at the experimental time scale, e.g. 0.001% w/w.

Formation of Chitosan/Lecithin Oil-in-Water Fibers

Fibers with a chitosan/lecithin shell can be formed by applying short duration mechanical forces at the beginning of the shell formation process, as described hereafter. They can be used as thickening agent after recovery.

1. A chitosan solution of concentration in the range 0.1-1% w/w is prepared by dispersion of a chitosan powder in water (average molecular weight Mw in the range 100,000 to 500,000 g/mol), deacetylation degree in the range 60-80%). Chloride acid is used to achieve proper dissolution, to set the pH at 3 (ideally).

2. Lecithin YN from is dissolved in mid-chain-triglyceride oil at a concentration in the range 0.1-0.5% w/w.

3. The lecithin YN solution formed in (2) is dispersed in the chitosan solution formed in (1) under high stress mechanical stirring using e.g. Polytron rotor-stator. An emulsion is formed by dispersing the lecithin YN oil solution formed in (2) in water at pH 3, for oil to water volume proportion typically in the range 1%-40%, using a mechanical dispersion method, typically a high-speed rotor-stator (of e.g. Polytron brand type). Since the interfacial tension is very low as soon as the membrane has started forming, the drops are very deformable and are stretched to fibers by the high shear forces.

4. The dispersion formed in (3) is left in quiescent state or kept under gentle mechanical stirring, which leaves the interfacial shell to grow in thickness, and sets the shape of the dispersed oil-in-water bodies to fibers with a biopolymer solid shell.

5. In the dispersion formed in (4), the capsule shell growth is stopped by setting the pH in the aqueous phase to 7 using sodium hydroxide.

6. From dispersion formed in (5), the fibers are then recovered by centrifugation/redispersion in pure water.

Formation of Chitosan/Lecithin YN Oil-in-Water Capsule with Composite Shell

Capsules and membranes can be formed in the presence of non-ionic emulsifiers, which was tested with 1% w/w of polysorbate (of which the commercial name is Tween 20). Such emulsifiers can be used in addition to the emulsifying properties of chitosan and lecithin YN, particularly if the shell formation needs to be decoupled from an emulsification step. The emulsifier can be chosen to be non-ionic in order to minimize interaction with the electrostatic supramolecular complexation mechanism.

This result confirms the possibility of forming membranes in the presence of small emulsifiers.

1. A chitosan solution of concentration in the range 0.1-1% w/w is prepared by dispersion of a chitosan powder in water (average molecular weight Mw in the range 100,000 to 500,000 g/mol), deacetylation degree in the range 60-80%). Chloride acid is used to achieve proper dissolution, to set the pH at 3 (ideally).

2. 1% w/w Tween 20 is dissolved in the solution formed in (1).

3. Lecithin YN from is dissolved in mid-chain-triglyceride oil at a concentration in the range 0.1-0.5% w/w.

4. An emulsion is formed by dispersing the lecithin YN oil solution formed in (3) in water at pH 3, for oil to water volume proportion typically in the range 1%-40%, using a mechanical dispersion method, typically a high-speed rotor-stator (of e.g. Polytron brand type).

5. The emulsion formed in (4) is mixed with the chitosan solution prepared in (1) in 1:1 weight proportions, by soft mechanical mixing.

6. The dispersion formed in (5) is left in quiescent state or kept under gentle mechanical stirring, which leaves the interfacial shell to grow in thickness.

7. In the dispersion formed in (6), the capsule shell growth is stopped by setting the pH in the aqueous phase to 7 using sodium hydroxide.

Formation of Chitosan/Lecithin YN Oil-in-Water Capsules Around Mint Oil for Prolonged Freshness Sensation in Sweets Encapsulation of mint oil was done. The capsules dispersed in a sugar-based matrix impart enhanced as well as prolonged perception of the freshness due to the mint oil, owing to the muco-adhesiveness of the mint oil.

1. Using the method described in Example 1 by replacing MCT oil by mint oil, mint oil-in-water capsules are prepared, of size 1-20 micrometers in diameter.

2. The capsules are dispersed in a sugar-based matrix in powder form.

3. The powder is transformed in tablets.

Results of Lingering Freshness and Sweetness Perception:

24 naive participants took part to the sensory evaluation study. They evaluated the lingering intensity of refreshing/freshness and sweetness attributes perceived after the complete in-mouth dissolution of the tablet. Each attribute was evaluated 5 min, 15 min, 35 min, 45 min and 55 min after the product consumption. The products were coded and evaluated according to a balanced experimental design between subjects. Each subject evaluated one sample per day always at the same moment of the day. For each attribute, panel mean differences between products were calculated by a paired t-test (two-tailed). Confidence level was set to 95% for all analyses.

Figure 5:
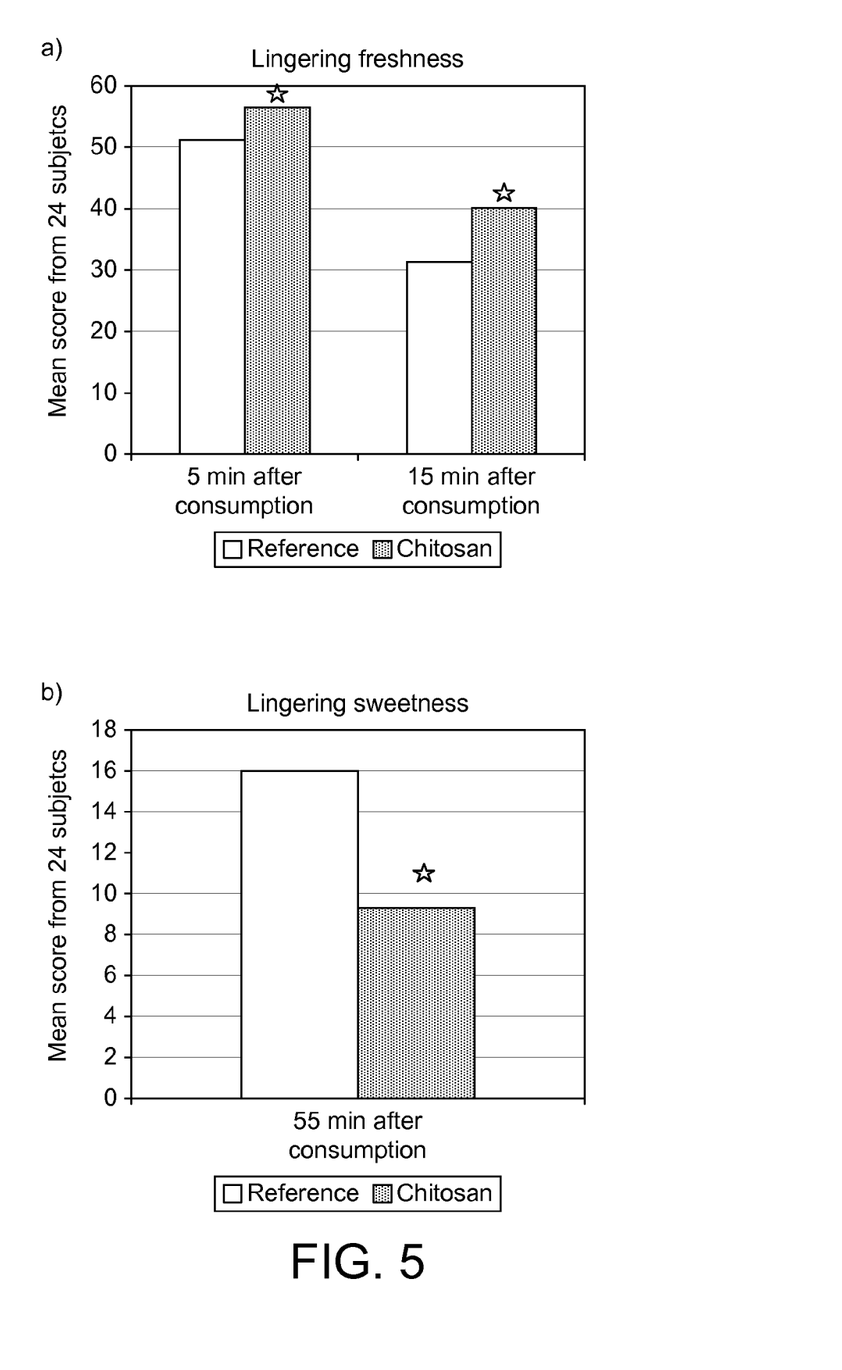
FIG. 5a shows the impact of chitosan on lingering freshness and FIG. 5b shows the impact of chitosan on lingering sweetness. A star means: significant difference between mean scores with p-value<0.05.

FIG. 5a shows that the lingering freshness was significantly higher after consumption of the mint tablet with chitosan than after consumption of the reference mint tablet (without chitosan) for times 5 min and 15 min. For the other evaluation times the freshness enhancing effect of chitosan was also observed but the effect was not significant.

FIG. 5b shows that the lingering sweetness was significantly lower 55 min after consumption of the mint tablet with chitosan than after consumption of the reference mint tablet (without chitosan). For the other evaluation times the sweetness reduction induced by chitosan was also observed but the effect was not significant.

The capsule shell thickness once again allows for a high enough mechanical strength to be achieved in order to process the capsules in a sugar-based matrix without disrupting them to lose the encapsulated material.

Figure 6:
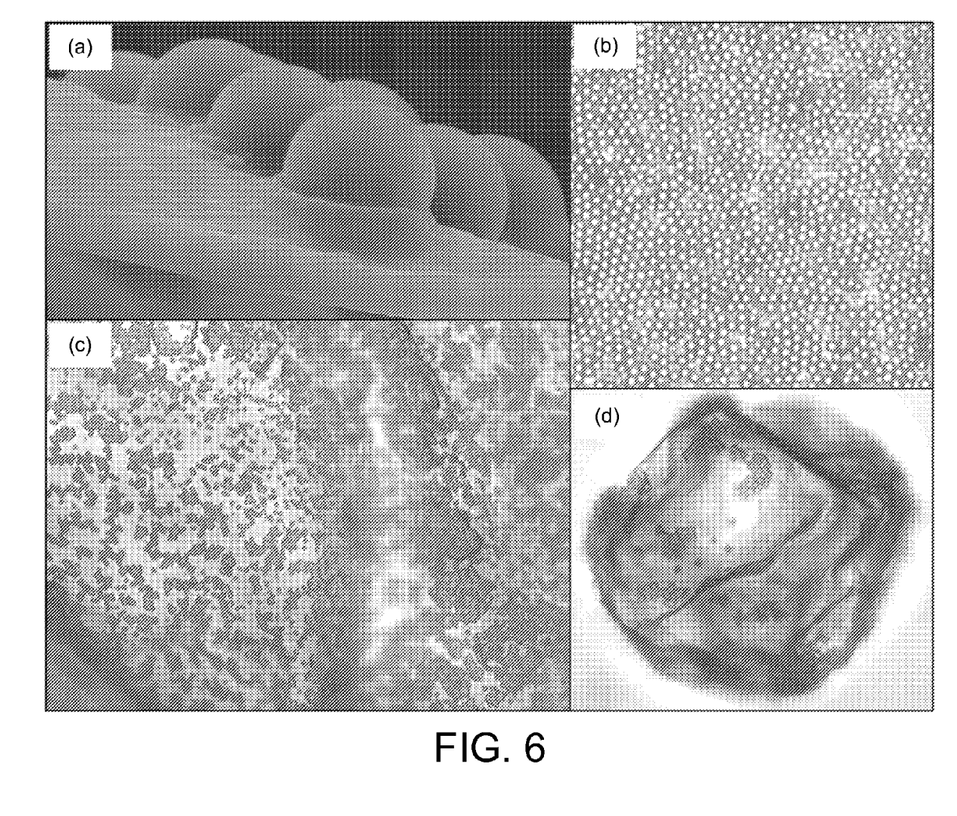
FIG. 6 shows a Chitosan/lecithin YN membrane and capsule with hydrophobic polystyrene particles (2.7 µm diameter) entrapped in, recovered in ethanol and dried. (a), (b), (c): large membrane. (a) SEM image. (b) Optical Microscopy (×50). (c) (×10). (d) Capsule "functionalized" with the same polystyrene particles.

Formation Chitosan/Lecithin YN Water-in-Oil Capsule with Particles Encased in the Capsule Shell Surface active particles can be captured at the membrane's surface, on the side of the hydrophobic phase—this for any particle hydrophobictiy—, by adhesive forces (FIG. 6). First a particle-laden water/oil interface is created in the absence of at least one of the complexants, then the membrane is formed at o/w the interface.

1. A chitosan solution of concentration in the range 0.1-1% w/w is prepared by dispersion of a chitosan powder in water (average molecular weight Mw in the range 100,000 to 500,000 g/mol), deacetylation degree in the range 60-80%. Chloride acid is used to achieve proper dissolution, to set the pH at 3 (ideally).

2. Lecithin YN from is dissolved in mid-chain-triglyceride (MCT) oil at a concentration in the range 0.1-0.5% w/w.

3. A dispersion of surface active particles, e.g. colloidal polystyrene particles (e.g. 2.7 micrometers in diameter, uncharged) in water (pH 3) or in a mixture of water and ethanol (typically 1:1 in volume), is prepared.

4. The dispersion prepared in (3) is mixed to the chitosan solution prepared in (1).

5. An emulsion is formed by dispersing the chitosan solution mixed with particles prepared in (4), with mid-chain-triglyceride oil, for water to oil volume proportion typically in the range 1%-40%, using a mechanical dispersion method, typically a high-speed rotor-stator (of e.g. Polytron brand type).

6. The emulsion prepared in (5) is left to age, until the particles adsorb to the oil/water interface (i.e. the surface of the drops).

7. The emulsion formed in (6) is mixed with the lecithin YN solution prepared in (2) in 1:1 weight proportions, by soft mechanical mixing.

8. The dispersion formed in (4) is left in quiescent state or kept under gentle mechanical stirring, which leaves the interfacial shell to grow in thickness.

9. In the dispersion formed in (5), the capsule shell growth is stopped by successive centrifugation/redispersion steps, with redispersion in pure MCT oil, until the concentration in lecithin YN is low enough for the formation kinetics to be practically stopped at the experimental time scale, e.g. 0.001% w/w.

For results see FIG. 6.

The invention claimed is:

1. A composition containing an oily fraction, a hydrophilic fraction, at least one body, the body comprising:
   a shell comprising at least 5 molecular layers adjacent to each other, and each of the 5 molecular layers comprising complex molecules comprising chitosan and at least one lipidic phosphatidic acid surfactant, the lipidic phosphatidic acid surfactant comprises at least 20% w/w of all lipidic surfactants present in the shell; and
   a content comprising an internal phase comprising at least one component selected from the group consisting of a hydrophilic component and a hydrophobic component.

2. The composition of claim 1, wherein the composition is an emulsion.

3. The composition of claim 1, wherein the internal phase comprises at least about 50 Vol-% of the content of the body.

4. The composition of claim 1, wherein the shell comprises chitosan and an lipidic phosphatidic acid surfactant at a ratio of 1:10 to 10:1.

5. The composition of claim 1, wherein the hydrophilic component of the content is liquid or gaseous.

6. The composition of claim 1, wherein the internal phase comprises an oil selected from the group consisting of a flavored oil; fragranced oil; essential oils; fish oil; omega-3 fatty acids; and omega-6 fatty acids.

7. The composition of claim 1, wherein the hydrophilic component is selected from the group consisting of hydrophilic liquids, fruit juices, lemonades, alcoholic beverages, coffee liquors, coffee extracts, flavoured waters, proteins, enzymes, water-soluble vitamins, and combinations thereof.

8. The composition of claim 1, wherein the body comprises chitosan in an amount comprising about 0.01-1 weight-% of the body.

9. The composition of claim 1, wherein the lipidic phosphatidic acid surfactant has a partition coefficient (water/oil) of less than 1:100 in ambient conditions.

10. The composition of claim 1, wherein the body comprises particles that adsorb on a water/oil interface, encased in its shell and protruding at the hydrophobic side of the shell, the particles are selected from the group consisting of coloring agents, tastants, antioxidants, antibacterial agents, radical scavengers, fat particles, mineral particles, charged molecules, and combinations thereof.

11. Method to produce the composition of claim 1 comprising the steps of
   combining at least one lipidic phosphatidic acid surfactant with an oily fraction to produce a solution A;
   combining chitosan with the hydrophilic fraction to produce a solution B;
   mixing solutions A and B, to prepare dispersion C; and
   allowing the shell to form.

12. Method of claim 11 comprising the step of stopping growth of the shell.

13. Method of claim 11 comprising applying flowing, shearing, or squeezing forces to the dispersion C.

14. Method of claim 11 comprising the step of allowing dispersion C to dry out.

15. The composition of claim 1, wherein the body has a form selected from the group consisting of a substantially round capsule, an elongated capsule, a flat-shape capsule and a fiber.

16. The composition of claim 1, wherein the shell comprises a thickness of at least 100 nm in the wet state.

* * * * *